(12) United States Patent
Tsai et al.

(10) Patent No.: US 8,431,399 B2
(45) Date of Patent: Apr. 30, 2013

(54) METHOD TO RESTORE CARTILAGINOUS PHENOTYPE OF CHONDROCYTES AFTER CULTURED AND EXPANDED IN VITRO

(75) Inventors: Yu-Hui Tsai, Taipei County (TW); Li-Hsuan Chiu, Taipei (TW); Chin-Chean Wong, Taipei (TW); Wen-Fu Lai, Taipei (TW); Shih-Ching Chen, Taipei (TW)

(73) Assignee: Taipei Medical University, Taipei (TW)

( * ) Notice: Subject to any disclaimer, the term of this patent is extended or adjusted under 35 U.S.C. 154(b) by 223 days.

(21) Appl. No.: 12/716,141

(22) Filed: Mar. 2, 2010

(65) Prior Publication Data

US 2011/0217773 A1    Sep. 8, 2011

(51) Int. Cl.
*C12N 5/00* (2006.01)
*C12N 5/02* (2006.01)

(52) U.S. Cl.
USPC .......................... 435/377; 435/404; 435/405

(58) Field of Classification Search .................. None
See application file for complete search history.

(56) References Cited

U.S. PATENT DOCUMENTS

| | | |
|---|---|---|
| 6,623,963 B1 | 9/2003 | Muller et al. |
| 7,189,567 B2 | 3/2007 | Yanaga |
| 7,273,756 B2 | 9/2007 | Adkisson et al. |

OTHER PUBLICATIONS

Taylor et al., Tissue Eng Part A. Feb. 2010;16(2):643-651.*
Ahmed et al., Tissue Eng Part A. Mar. 2009;15(3):665-673.*
Oesser et al., Cell Tiss. Res. 311:393-399, 2003.*
Bonaventure J, Kadhom N, Cohen-Solal L, Ng KH, Bourguignon J, Lasselin C, Freisinger P, 1994. Reexpression of cartilage-specific genes by dedifferentiated human articular chondrocytes cultured in alginate beads. Exp Cell Res. 212:97-104.
Lemare F, Steimberg N, Le Griel C, Demignot S, Adolphe M, 1998, Dedifferentiated chondrocytes cultured in alginate beads: restoration of the differentiated phenotype and of the metabolic responses to interleukin-1beta. J Cell Physiol. 176:303-313.
Yaeger PC, Masi TL, de Ortiz JL, Binette F, Tubo R, McPherson JM, 1997. Synergistic action of transforming growth factor-beta and insulin-like growth factor-I induces expression of type II collagen and aggrecan genes in adult human articular chondrocytes. Exp Cell Res. 237:318-325.

* cited by examiner

*Primary Examiner* — Daniel C Gamett
(74) *Attorney, Agent, or Firm* — WPAT, P.C.; Anthony King (57) ABSTRACT

The present invention provides a method for restoring native chondrocyte phenotype and functions of, and/or increasing type II collagen as well as aggrecan mRNA expression levels and GAG accumulation level in dedifferentiated chondrocytes which have been subcultured and expanded in vitro, which comprising culturing the said dedifferentiated chondrocytes in vitro with a medium comprising type II collagen, or its biologically active peptide fragment(s) or analogs with or without growth factor(s), wherein the type II collagen or its biologically active peptide fragment(s) or analogs are effective to restore chondrocyte phenotype and functions of, and/ or to increase type II collagen and aggrecan expression levels and GAG accumulation level in the said dedifferentiated chondrocytes.

20 Claims, 9 Drawing Sheets

METHOD TO RESTORE CARTILAGINOUS PHENOTYPE OF CHONDROCYTES AFTER CULTURED AND EXPANDED IN VITRO

FIELD OF THE INVENTION

The present invention relates to a method of restoring chondrocyte phenotype in dedifferentiated chondrocytes. Particularly, the chondrocytes produced from the invention are suitable for cartilage repair.

BACKGROUND OF THE INVENTION

Articular cartilage is composed of chondrocytes encased within the complex extracellular matrix produced by these cells. The unique biochemical composition of this matrix provides for the smooth, nearly frictionless motion of articulating surfaces of the knee joint. With age, tensile properties of human articular cartilage change as a result of biochemical changes. After the third decade of life, the tensile strength of articular cartilage decreases markedly. Damage of cartilage caused by trauma or disease, e.g., rheumatoid and osteoarthritis, can lead to serious physical debilitation. The repair of defective cartilages has been improved recently by transplantation of autogenous or allogenous chondrocytes, or through the use of mesenchymal stem cells.[1-4] Moreover, U.S. Pat. No. 6,623,963 discloses a biocompatible, resorbable Type II collagen-based matrix is reconstituted from solubilized animal cartilage tissue and used in the culture and growth of cells, such as chondrocyte cells. However, the limited source for sufficient amount of normal tissues or cells restricts the development and clinical application of these cell-based therapies. Moreover, during in vitro monolayer expansion of harvested chondrocytes, the cells are eventually lose their phenotypic features, such as attenuation of type II collagen production and reduction in proteoglycan accumulation.[5,6]

These cellular alterations are probably resulted from changes in chondrocyte functions or the reduced ability of these cells to maintain normal synthetic activity during serial monolayer culture. Less uniform aggrecan and functional proteins, and altered responsiveness to anabolic growth factors, such as transforming growth factor β1 (TGF-β1) and insulin-like growth factor I (IGF-I)[7-9] were observed in these cells. The collagen typing of the progeny has been shown to shift from type II to type I collagen during the rapid proliferation to quiescence.[5,6] Almost invariably, the serially expanded chondrocytes do not retain their original round or polygonal appearance, but gradually become fibroblast-like cells, and then fully extended and flattened on the substratum during monolayer expansion. This kind of chondrocytes was referred as 'dedifferentiated' since it no longer possesses the general phenotypic features and functions of freshly harvested chondrocytes.[5,6] Numerous factors, including the seeding density, culture medium and age of the cell source, affect the extent and rate of this process.[10,11] Loss of chondrocyte phenotype and functions during serial expansion in vitro poses a key limitation to the commercialization and/or clinical use of the orthobiologic approaches of cartilage repair.

The two major extracellular components of articular cartilage are the aggregated proteoglycan consisting aggrecan, and type II collagen. The type II collagen forms the backbone of cartilage, providing it with stability and tensile strength. The highly hydrated proteoglycan component is responsible for the compressive stiffness of cartilage. In addition to playing an important structural framework, the extracellular matrix (ECM) component has also been shown to contribute to the regulation of chondrocytes through cell-surface signaling mechanisms.[15-17] These complex interactions would influence chondrocyte gene expression at mRNA levels as well as protein levels, thereby changing the internal status of the cell through its display of surface receptors and ECM molecules.[17] Matrix deterioration often associated with the pathological state of the cartilage, in which type II collagen is reduced and activity of metalloproteinases increased.[8,9] Furthermore, TGF-β1 and IGF-I have been implicated as important mediators in the induction and maintenance of matrix macromolecules in articular cartilage.[4,18-21]

Loss of chondrocyte phenotype during serial expansion in vitro poses a key limitation to the commercialization and/or clinical use of orthobiologic approaches to articular cartilage repair. To counter dedifferentiation, chondrocytes traditionally have been suspended in three-dimensional environments such as hydrogels, e.g., agarose or alginate, pellet culture, or three-dimensional scaffolds. Several approaches for chondrocyte redifferentiation have been developed. Some studies demonstrated that 'dedifferentiated' chondrocytes could be 'redifferentiated' while cultured three-dimensionally in gels of agarose, collagen or alginate.[8,12-14] However, using this method, only the chondrocytes subcultured up to passage 4 (P4) can be restored to express cartilaginous phenotype. Accordingly, the numbers of expanded chondrocytes which are still retaining the ability to restore native chondrocyte phenotype can only be achieved at about $2^{3.8}$ folds of expansion of the original cell number, which are insufficient for commercial and/or clinical use. Furthermore, the procedure for three-dimensional culture in alginate bead is complex and may take at least two weeks to induce restoration of cartilaginous phenotype. Moreover, the chondrocytes need to be isolated from alginate beads for further applications, such as autogenous or allogenous transplantation. All the above disadvantages make the three-dimensional methods ineffective.

U.S. Pat. No. 7,273,756 discloses a method of maintaining chondrocyte phenotype during serial expansion by culturing a population of chondrocytes in a defined serum-free culture medium containing cytokines and on a substrate that is modified by covalent attachment of hyaluronic acid. U.S. Pat. No. 7,189,567 provides a method for rapidly culturing a large amount of human chondrocytes to give normal chondrocytes or a mass thereof, comprising co-culturing human chondrocytes together with perichondral cells in the chondrogenic stage, as feeder cells, which support the proliferation ability of the chondrocytes, to allow rapid culturing of the human chondrocytes in a large amount. Yaeger P. C. et al. demonstrated that synergistic action of TGF-β1 and IGF-I induces expression of type II collagen and aggrecan genes in adult human articular chondrocytes.[30] However, addition of cytokines, hyaluronic acid or growth factors for restoration of chondrocyte phenotype in chondrocyte cell culture is cost ineffective. Furthermore, only the chondrocytes subcultured up to passage 4 (P4) can be restored to express cartilaginous phenotype, and the cells of the subsequent passages cannot be redifferentiated. Accordingly, the numbers of redifferentiated chondrocytes can only achieve about $2^{3.8}$ folds of the original number, which is insufficient for commercial and/or clinical use.

In view of the above, there exists a need for a convenient and effective method for restoring phenotypic expression of expanded chondrocytes.

SUMMARY OF THE INVENTION

The present invention provides a method for restoring native chondrocyte phenotype and functions of and/or increasing type II collagen and AGN expression levels and GAG accumulation in dedifferentiated chondrocytes which have been subcultured and expanded in vitro, which comprising culturing the said dedifferentiated chondrocytes in vitro with a medium comprising type II collagen or its biologically active peptide fragment(s) or analogs to restore native chondrocyte phenotype and functions of, and/or increasing type II collagen and AGN expression levels and GAG accumulation level in dedifferentiated chondrocytes.

BRIEF DESCRIPTION OF THE DRAWING

FIG. 6 shows the mRNA expressions of type I and type II collagens, aggrecan and GAPDH in P9 rabbit chondrocytes after treated with various agents. P9 rabbit chondrocytes cultured in 6 well plates were treated with or without either exogenous COL II or in combination with designated growth factors for 6 days. Designated sets of primer sequences for COL1A1, COL2A1, AGN and GADPH were listed in Table 1. In the presence of COL II, chondrocyte specific differentiation marker COL2A1 was greatly re-expressed in either P9 control (COL II+, P9 Control) or P9 cells treated with TGF-β1 plus IGF-I group (COL II+, T+IGF-I). However, the COL2A1 expression was reduced in P9 cells treated with COL II plus TGF-β1 (COL II+, TGF-β1). On the contrary, in the absence of COL II (COL II−), no COL2A1 expression was detected in the P9 control group (COL II−, P9 Control). However, COL2A1 were re-expressed in either TGF-β1 or TGF-β1 plus IGF-I treated groups, despite the absence of exogenous COL II. Furthermore, the mRNA expression of AGN was only found in the P9 cells treated with TGF-β1 plus IGF-I in the presence of COL II, as was in the P1 control cells. This RT-PCR graph is a representative of triplicate experiments.

DETAILED DESCRIPTION OF THE INVENTION

The present invention discovers that chondrocyte phenotype of dedifferentiated chondrocyte after extensive expanding can be restored by culturing in a medium containing type II collagen. It discovers that collagen, alone or in combination with growth factors, can restore the native chondrocyte phenotype and functions of the dedifferentiated chondrocytes which have been subcultured in vitro for several passages.

DEFINITION

Unless otherwise defined herein, scientific and technical terms used in connection with the present invention shall have the meanings that are commonly understood by those of ordinary skill in the art. The meaning and scope of the terms should be clear; however, in the event of any latent ambiguity, definitions provided herein take precedence over any dictionary or extrinsic definition.

The term "chondrocyte" or "chondrocytes" denotes cells found in various types of cartilage, e.g., hyaline cartilage, elastic cartilage, and fibrocartilage. Chondrocytes are mesenchymal cells that have a characteristic phenotype based primarily on the type of extracellular matrix they produce. Precursor cells produce great level of type I collagen, but when they become committed to the chondrocyte lineage, their synthesis of type I collagen declined, and start synthesizing type II collagen which constitutes a substantial portion of the extracellular matrix. In addition, committed chondrocytes produce proteoglycan aggregate, called aggrecan, which has glycosaminoglycans that are highly sulfated. They refer to cells that are capable of expressing characteristic biochemical markers of chondrocytes, including but not limited to collagen type II, chondroitin sulfate, keratin sulfate and characteristic 3-D or in-tissue morphologic features, including but not limited to the rounded morphology observed in 3-D culture, and ability to secrete collagen type II, including but not limited to the generation of tissue or matrices with hemodynamic properties of cartilage in vitro.

The term "chondrocyte phenotype" refers to a cell that has (i) a spherical shape and the ability to synthesize and accumulate within the matrix significant amounts of (ii) aggrecan and (iii) type II collagen without (iv) accumulating within the matrix an effective amount of type I collagen. That is, the cell retains the differentiated state and functions of native chondrocytes, rounded morphology and hyaline cartilage gene expression, etc.

The term "dedifferentiated" as used herein is to describe cells that lack their differentiated functions. For example, when chondrocytes of cartilage tissue are released from the cartilage matrix, placed in a monolayer culture and subcultured extensively, they stop producing characteristic markers that define them as being the differentiated chondrocytes. Two such markers for differentiated chondrocytes are two well characterized structural macromolecules, cartilage proteoglycan and type II collagen. The dedifferentiated chondrocytes are the chondrocytes which lose their chondrocyte phenotype to become dedifferentiated chondrocytes after they have been subcultured and expanded for more than three passages.

The term "expanding", "expanded", or "expand" as used herein refers to the process or growing cells in quantity by proliferation in vitro.

Restoration of Native Chondrocyte Phenotype and functions of, and/or Increase of Aggrecan (AGN) and Type II Collagen Expression Levels and Glycosaminoglycan (GAG) Accumulation in Dedifferentiated Chondrocytes In one aspect, the present invention provides a method for restoring native chondrocyte phenotype and functions of, and/or increasing type II collagen and AGN expression levels and GAG accumulation in the dedifferentiated chondrocytes which have been subcultured and expanded in vitro, which comprising culturing the said dedifferentiated chondrocytes in vitro with a medium comprising type II collagen or its biologically active peptide fragment(s) or analogs to restore native chondrocyte phenotype and functions of, and/or increasing type II collagen and AGN expression levels and GAG accumulation level in dedifferentiated chondrocytes. According to the invention, the type II collagen or its biologically active peptide fragment(s) or analogs are effective to restore chondrocyte phenotype and functions of, and/or to increase type II collagen and AGN expression levels and GAG accumulation in the said dedifferentiated chondrocytes. In one embodiment, the medium can further comprise one or more growth factor(s). According to the invention, the addition of growth factor can improve the restorating extent of phenotype and functions of the dedifferentiated chondrocytes, and/or increase type II collagen and GAG expression levels in dedifferentiated chondrocytes.

During the process of expanding the cell population in vitro, chondrocytes usually undergo phenotypic transformation or dedifferentiation. Morphologically, the cells resemble fibroblasts. Synthesis of type II collagen and aggrecan is gradually diminished and synthesis of type I collagen, typical of fibrocartilage, is increased. Limited data exist to support the contention that the cells redifferentiate in situ following implantation. Reestablishment of the chondrocytic phenotype is critical to the success of the repair process, as tissue produced by dedifferentiated chondrocytes which are phenotypically fibroblastic functions poorly as a replacement for articular cartilage.

GAG (glycosaminoglycan) synthesis ability represents the anabolic activity of cultivated chondrocytes. GAG and type II collagen are two characteristic macromolecules that have been used to define differentiated chondrocyte phenotype. The present invention found that type II collagen, with or without growth factor, can restore native chondrocyte phenotype of, and/or increase GAG and type II collagen expression levels in dedifferentiated chondrocytes. The combination of type II collagen and growth factor(s) exhibits synergistic effect on restoring native chondrocyte phenotype and functions of, and/or increasing AGN (aggrecan) and type II collagen expression levels and GAG accumulation level in the restored dedifferentiated chondrocytes.

According to the invention, chondrocytes can be isolated from cartilagenous tissues of either juveniles or adults. Additional sources of chondroprogenitor cells include, without limitation, mesenchymal stem cells, umbilical cord stem cells, bone marrow stromal cells, adipose stromal cells or chondrogenic progenitor cells derived from periosteum or synovium. Chondrocytes can be isolated from the autologous healthy part of the patient's cartilage, allologous cartilage of other human's, or xenologous cartilage of any other mammal's, including, without limitation, livestock (such as cow, pig, sheep and horse etc.), orangutan, chimpanzee, monkey, dog, cat, rabbit, rat, mouse, etc. Chondrocytes can also be derived from transgenic animals that have been genetically engineered to prevent immune-mediated xenograft rejection. In some aspects, cartilage can be obtained from any tissue containing hyaline, elastic or fibro-cartilage.

According to the invention, any medium capable of supporting cells in tissue culture may be used to subculture and expand chondrocytes. Media formulations that will support the growth of fibroblasts and/or chondrocytes include, but are not limited to, Dulbecco's Modified Eagle's Medium (DMEM), Dulbecco's Modified Eagle's Medium/Ham's Nutrient Mixture F12 (DMEM/F12), alpha modified Minimal Essential Medium ($\alpha$-MEM), and Roswell Park Memorial Institute Media 1640 (RPMI Media 1640) and the like. Typically, 0 to 20% Fetal Bovine Serum (FBS) or 1-20% horse serum is added to the above media in order to support the growth of chondrocytes. However, a defined medium could be used if the necessary growth factors, cytokines, and hormones in FBS for stromal cells and chondrocytes are identified and provided at appropriate concentrations in the growth medium. Media useful in the methods of the invention may contain one or more compounds of interest, including, but not limited to, antibiotics, and mitogenic or differentiative compounds for stromal cells. The cells will be grown at appropriate temperature (such as 37° C.) in a humidified $CO_2$-incubator. The carbon dioxide content will be maintained between 2% to 10% and the oxygen content between 1% and 22%. After chondrocytes are cultured for several passages, they gradually lose their anabolic activity and become quiescent; their phenotype changed and they become dedifferentiated.

According to the invention, it is found that the native phenotype and functions, type II collagen and AGN mRNA expression levels, and GAG accumulation level of the said dedifferentiated chondrocytes can be restored by culturing them with type II collagen, or its biologically active peptide fragment(s) or analogs which are capable of restoring the native phenotype and functions of chondrocytes. According to the invention, the term "active fragment" of type II collagen describes any synthetic peptide or polypeptide construct containing one or more partial amino acid sequences of the type II collagen and possessing the ability to restore chondrocyte phenotype and functions of, and/or increase type II collagen and GAG expression levels and GAG accumulation level in the dedifferentiated chondrocytes. The term "active analogs" of type II collagen include compounds that are structurally related to the type II collagen or to active fragments thereof. As such, the term includes, without limitation, any combination of their polypeptide domains or fragments possessing the ability to restore native chondrocyte phenotype and functions of the said dedifferentiated chondrocytes. The term "analog" also encompasses any polypeptide which differs from the amino acid sequence of the type II collagen while still retaining substantially equivalent ability to restore native chondrocyte phenotype and functions of the dedifferentiated chondrocytes. According to the invention, the concentration of type II collagen, its biologically active peptide fragment(s) or analogs ranges from 50 to 1,000 µg/ml, preferably 50 to 800 µg/ml, 50 to 600 µg/ml, 50 to 400 µg/ml, 50 to 200 µg/ml; 100 to 800 µg/ml, 100 to 600 µg/ml, 100 to 400 µg/ml, 100 to 200 µg/ml; 200 to 600 µg/ml or 200 to 400 µg/ml, and most preferably 200 to 400 µg/ml.

According to the invention, the dedifferentiated chondrocytes are the chondrocytes which lose their chondrocyte phenotype and functions to become dedifferentiated chondrocytes after they are extensively subcultured for far more than three passages. Preferably, they are subcultured and expanded for more than four passages, more preferably, five, six, seven or eight passages. Most preferably, they are subcultured and expanded for at least eight passages. The subculture of chordrocytes is to have enough cells for subsequent clinical applications. During each subculture process, the cells are expanded 3-4 times. However, they will lose their phenotype and functions after extensive subculture.

In one preferred embodiment, growth factor(s) can be further added to the medium with type II collagen to further improve the restoration of phenotype and functions of the dedifferentiated chondrocytes, and/or increase type II collagen and AGN expression levels and GAG accumulation level in the dedifferentiated chondrocytes. Furthermore, the combination of type II collagen and growth factor(s) may exhibit synergistic effect on the restoration of chondrogenic phenotype and functions of the dedifferentiated chondrocytes, and/or the increase of type II collagen and AGN expression levels and GAG accumulatin level in the restored dedifferentiated chondrocytes. A growth factor is a substance capable of stimulating cellular growth, proliferation and cellular differentiation. Examples are cytokines and hormones that bind to specific receptors on the surface of their target cells. Preferably, the growth factors used in the invention are, but not limited to, bone morphogenetic proteins (BMP), transforming growth factor (TGF), insulin-like growth factors (IGF), fibroblast growth factor (FGF), platelet-derived growth factor (PDGF), growth/differentiation factor (GDF), epidermal growth factor (EGF), vascular endothelial growth factor (VEGF) or the combination thereof. More preferably, the growth factor are transforming growth factors (TGF), insulin-like growth factors (IGF), fibroblast growth factors (FGF), bone morphogenetic proteins (BMP) or their combinations thereof. Most preferable is insulin-like growth factor (IGF), in combination with transforming growth factor (TGF), or with fibroblast Growth factor (FGF); or the combination of IGF, TGF and FGF. Most preferable is insulin-like growth factor-1 (IGF-1), in combination with transforming growth factor beta-1 (TGF-β1), or with fibroblast Growth factor-2 (FGF-2); or the combination of IGF-1, TGF-β1 and FGF-2.

In another embodiment, type I collagen can be further used to increase total GAG expression level of the dedifferentiated chondrocytes. By adding type I collagen, the cell proliferation or total cell number can be increased so that the total GAG expression level is increased. In another further embodiment, other components beneficial to restore chondrocyte phenotype known in the art may be further added. Examples of the components include but not limited to cytokine and hyaluronic acid.

According to the invention, the dedifferentiated chondrocytes are cultured with type II collagen in two-dimensional (2D) or three-dimensional (3D) cell culture. The 2D cell culture is a traditional approach for most cells. It is typically performed using a petri dish or culture bottle filled with a small volume of nutrient media and placed within a temperature controlled, humidified $CO_2$-incubator. The cells within the dish or bottle exchange gases with the ambient gas atmosphere within the incubator. In 2D cell culture, cells typically grow on the bottom of the container or on the surface of the media.

The 3D cell culture system is applicable to proliferation of different types of cells and the formation of a number of different tissues. It uses a cell culture substrate comprising elements necessary for a normal cell to form a competent extracellular matrix when in culture. Cell culture matrices for 3D culture can be anything from ECM proteins, to naturally-derived basement membranes, to nature biological polymers, to semi-synthetic or synthetic hydrogels, to fractured polystyrene to electrospum fibers. etc.

Proliferation of Dedifferentiated Chondrocytes

In another aspect, the method of the invention can further comprises a step of adding type I collagen to the medium to increase the proliferation of chondrocytes. It is found that type I collagen can increase the proliferation of chondrocytes. By adding type I collagen to increase cell numbers of chondrocytes, the amounts of type II collagen used in the restoration of native chondrocyte phenotype can be reduced. Preferably, the ratio of type I to type II collagen ranges from 1:1 to 0.1:9.9. More preferably, the ratio of type I to type II collagen ranges from 1:2 to 0.1:9.9. Most preferably, the ratio of type I to type II collagen is 1:2 to 1:6, 1:2 to 1:5, 1:2 to 1:4 or 1:2 to 1:3.

Utility

The present invention provides a method devoid of the disadvantages of the prior art. Specifically, the method of the present invention avoids the complex subculture procedure of using alginate beads, and continuous addition of cytokines or hyaluronic acid. In accordance with the method of the invention, the chondrocytes can be cultured in two-dimensional plates and directly used for further application without isolation. In addition, in accordance with the method of the invention, there is no need to add expensive cytokines or hyaluronic acid into cell culture during cell expansion. The present invention identifies the phenotypic significances of cellular microenvironments. The effects of growth factors and collagens on cell morphology, proliferation rate, glycosaminoglycan (GAG) level, and collagen and aggrecan (AGN) gene expressions of near quiescent passage 7 (P7) and passage 9 (P9) dedifferentiated articular chondrocytes were carefully analyzed. Furthermore, the superior efficiency of type II collagen to type I collagen in restoring human P7 chondrocyte function in 3-D constructs were also investigated.

The human chondrocytes or the cell mass obtained by the invention is integrated into a biomaterial and used for transplant as a cartilage therapy material. Examples of biomaterials into which human chondrocytes or their cell mass may be integrated include: collagen, polyglycolic acid (PGA), polylactic acid (PLA), alginate, polyethylene oxide, fibrin adhesive, polylactic acid-polyglycolic acid copolymer, proteoglycans, glycosaminoglycans and human dermis, which may be used independently or in combination. Proteoglycans and glycosaminoglycans maybe sulfated. Those biomaterials separate the chondrocytes from the surroundings and prevent the transplanted chondrocytes from diffusing or being rapidly absorbed, and preferably can serve as a scaffold for the transplanted chondrocytes. The biomaterials can be in any form, for example, membrane such as sheet, porous bodies such as sponges, meshes such as knits, textiles, non-woven fabrics, cotton and the like. It is preferable to use a porous material because this will allow the chondrocytes to more easily adhere to the biomaterial and infiltrate inside to promote the formation of cartilage tissue.

A further objective of this invention is also to utilize the chondrocytes produced by the process described above, or a composition described above, to prepare a composition intended for the implantation of chondrocytes in human beings, particularly to treat cartilaginous defects. The term "treat cartilaginous defects" designates, notably, the restoration or compensation of cartilaginous defects, which is to say particularly at least partial reconstitution of cartilage in the areas where it is defective. Preferably, this concerns utilization in an autologous context, that is, that the biological sample utilized in producing the chondrocytes comes from the subject to whom the chondrocytes that are produced will be administered.

The following examples are provided to aid those skilled in the art in practicing the present invention. Even so, the examples should not be construed to unduly limit the present invention as modifications to and variations on the embodiments discussed herein may be made by those having ordinary skill in the art without departing from the spirit or scope of the present inventive discovery.

EXAMPLES

Materials and Methods

Chondrocyte Isolation, Cultivation & Storage

A 3-day old New Zealand white rabbit was sacrificed in a CO2 chamber without pain, according to American Veterinary Medical Association's (AVMA) Guidelines on Euthanasia. Furthermore, the use of $CO_2$ chamber to sacrifice rabbit or rodents to obtain articular chondrocytes has also been described in the literature.[27,28] The Institutional Approval Certificate for Experimental Animal Usage is registered in Taipei Medical University as LAC-92-0036.

The full depth-articular cartilages from rabbit hip, knee, elbow and shoulder joints were harvested. Human chondrocyte were harvested from the healthy part of the articular cartilage slices that was discarded as medical wastes during the joint replacement surgery. The harvested cartilages were placed in chilled Hank's solution containing 3× concentrations of antibiotics including penicillin, streptomycin and fungizone (P/S/F). After several washings, the tissues were aseptically sliced into little pieces and digested with enzyme solution containing collagenase (1 mg/ml), hyaluronidase (1 mg/ml) and trypsin (12.5%) (Sigma, St. Louis, Mo.) at 37° C. with constant shaking for 1 hour. This step was repeated 3-4 times. Finally, the enzyme-released cells were combined, centrifuged and resuspended in Dulbecco's Modified Eagle's medium/F12 (DMEM/F12, Hyclone, Logan, Utah, USA) containing 10% fetal bovine serum (FBS, Gibco, Grand island, N.Y., USA), 40 mM L-proline and 3× P/S/F. Cells were plated at a density of $5\times10^5$ cells/10 cm dish in 10 ml of culture medium. The cells were then cultured in a 5% $CO_2$, and 90% humidity incubator at 37° C. for several days until reached confluence.

To grossly expand the cell population, cells from each dish were trypsinized and passaged into 3-4 plates of 10 cm dishes. Confluent cells from each dish were around 2-3 million. About 4-7 plates of cells from passage 3 on were then cryopreserved in medium containing 10% DMSO, depending on the plenty of cells, and stored in liquid nitrogen for later use. To thaw the frozen cells, the cryovials were placed in 37° C. water bath for one minute, and cells are immediately suspended in 10 ml of medium and spun down. The cell pellet is then resuspended in 10 ml of medium for subsequent cultivation.

For experiment, the cells were grown to confluence, trypsinized and subcultured in new dishes repetitively until the cells reached passage 8 or more. Cell morphology was observed throughout the entire culture interval using inverted light microscope (Olympus). Morphological changes, such as cell shapes, sizes, cell number and general health status were recorded using a digital camera (Nikon coolpix 4500) at both 160× and 400× magnifications on the first, third and sixth days of each passage. Cell numbers of each group of triplicate wells were counted with a hemocytometer (Burker, Marienfeld, Germany) under light microscope (Olympus) at a magnification of 400×. To accurately assess total live cell number, trypan-blue exclusion method was performed prior to cell counting with hemocytometer. Triplicate aliquots from each well of the group were counted to minimize variation.

Isolation of Type I & Type II Collagens

Bovine Type I collagen was used in the monolayer culture experiments of P9 rabbit chondrocytes. Crude extract of bovine skin collagen was obtained from TaiSalt R Incorporation (Taiwan), and was further digested with 3 mg/ml pepsin in 0.5 M acetic acid at 37° C. for 3 hours followed by salting out in 0.9M NaCl-0.5M acetic acid to obtain purified bovine type I collagen. The precipitated bovine type I collagen was washed several times with 70% ethanol in PBS to remove excessive salts and acid and to sterilize. On the other hand, type I collagen from rat tail tendon was also purified similarly as described previously[17,18] and applied in the 3-D culture study of human chondrocytes.

For the sufficient amount of collagen to establish the 3-D culture system, type II collagen used in both the monolayer and 3-D culture studies were isolated and purified from porcine sternum cartilage as previously described.[17,18] The minced cartilage pieces were pretreated with 4M guanidine HCl; followed by 4.5M NaCl-50 mM Tris, pH7.5. Then, the tissue was extracted with 3 mg/ml pepsin in 0.5 M acetic acid followed by salting-out in 0.9 M NaCl-0.5 M acetic acid. The type II collagen pellets were washed three times with 70% ethanol in PBS to remove excessive salts and acid, and also to sterilize. Finally, the collagen pellets were dissolved in 5 mM acetic acid, quantified and stored in 4° C. until use.

Effects of Microenvironmental Factors on Chondrocytes

Three plates of P8 chondrocytes at 80% confluence in passage 8 were trypsinized, pooled together and counted using a hemocytometer. Then, the cell suspension was divided equally into 6 aliquots, centrifuged and the residual medium was removed. The cell pellets were resuspended in medium containing 0, 50, 100, 200, 400 or 600 μg/ml of the following matrices: type I collagen (COL I, from bovine skin), type II collagen (COL II, from porcine cartilage), or various compositions of COL I and COL II collagen at a ratio of 1:1 or 1:2.

In addition, similar to the same protocol described above, portions of the cell pellets were re-suspended in medium containing premixed 200 µg/ml COL II, with either 2 ng/ml TGF-β1 or 2 ng/ml TGF-β1 plus 100 ng/ml IGF-I (R&D Systems, Inc. Minneapolis, Minn., USA). In the counterpart groups, those cells were re-suspended in respective media without exogenous COL II. The concentrations of TGF-β1 and IGF-I were similar to those described in the relevant literatures which study the effects of TGF-β1 and IGF-I on chondrocytes in monolayer cultures.[13,19] Finally, aliquots of $2\times10^4$ cells/well were plated in each well of 6-well cell culture dishes and cultured for 6 days with medium change every 3 days.

Glycosaminoglycan (GAG) Analysis by Alcian Blue Staining

Total GAG accumulation level was measured by alcian blue staining. Briefly, cells were rinsed thoroughly with phosphate buffered saline (PBS) and fixed with 10% formaldehyde for at least 30 minutes. After rinsed with distilled water, cells were washed with 0.018M $H_2SO_4$ for 30 minutes and drained completely. Alcian blue solution (1% alcian blue 8 GX in 0.018M $H_2SO_4$) was added to stain GAG for 3 hours. Then, the cells were immediately incubated with 0.018M $H_2SO_4$ for another 3 hours to remove redundant dye. Finally, the bound dye was eluted with dissociation buffer (4 M guanidine hydrochloride with 33% n-propanol, Sigma, St. Louis, Mo.). Using dissociation buffer as blank, the absorbance of all samples at 600 nm were measured using a spectrophotometer (Hitachi, U2000).

Total RNA Isolation & Semi-Quantitative RT-PCR

Total RNA was extracted by using TRIzol reagent as described by the manufacturer (Life Technologies Ltd., Paisley, UK) and stored at −80° C. until use. RNA (500 ng) was then reverse-transcribed in a 20 µl reaction mixture containing 1× Bca 1st buffer, 5 mM $MgSO_4$, 0.5 mM dNTPs, 2.5 µM oligo(dT) primer, 2.5 µM random 9 mers, 20 units of RNase inhibitor, and 22 units of BcaBEST polymerase (Takara Shuzo Co. Ltd., Tokyo, Japan). Reverse-transcription was performed according to the protocol described by the manufacturer. To reduce experimental variability, all RNA samples of the same group of experiment were subjected to reverse-transcription under the same conditions at the same time.

After RNA products were reverse-transcribed, aliquots of cDNA specimens in each group were further amplified by PCR using specific primer sets at the same time. The specific cDNA fragments were amplified by PCR using specific primer sets listed in Table 1. The PCR conditions were referred to the corresponding literatures.[20,21] The PCR products were electrophoretically separated on a 1.6% agarose gel at 100V/cm in TAE buffer containing ethidium bromide. The expression intensities of each cDNA were normalized by using GADPH cDNA product as internal control. The GADPH values were assessed by image analysis system (Kodak 1D 3.5) and also shown to be in the linear range of detection. The quantified same volumes of remaining cDNA samples in each group were subjected to PCR amplification for the determination of their relative levels of other cDNAs in each specimen and normalized with the respective GADPH cDNA level.

Redifferentiation of Chondrocytes in Three-Dimensional Cartilaginous Matrix

To determine the efficiency of type I and type II collagen in restoring the "dedifferentiated" chondrocyte phenotypes in a 3-D (three-dimensional) cartilaginous matrix, P7 human chondrocytes were suspended at $1\times10^6$ cells/ml of 2× concentration media, and mixed with an equal volume of 2 mg/ml type I collagen (COL I, from rat tail tendon) or type II collagen (COL II, from porcine cartilage) solution in 10 mM acetic acid. After polymerization of cell-collagen matrix at 37° C. for 24-48 hours, the cell-matrix constructs were transferred to a 25-T culture flask (Falcon, BD Bioscience™) and covered with 35 ml of DMEM/F12 medium containing 10% fetal bovine serum, 40 mM L-proline, 3× P/S/F. The medium was refreshed every 5 days. All samples were fixed on day 28 with PBS-balanced formalin, sectioned, and stained with hematoxylin/eosin (H&E) for histological evaluation and Safranin O staining for proteoglycan expression.

Statistical Analysis

Data from cell proliferation rates, accumulated GAG levels and semi-quantitative RT-PCR analyses were subjected to variance analysis (one-way ANOVA) and assessed as means±standard deviation (SD). Each experiment was performed in triplicates and repeated at least three times. Statistical significance was determined by Duncan multiple range test using chondrocytes cultured without any supplement as controls. Probability values $p<0.05$ were considered as significant and indicated with various alphabets in series.

Example 1

Chondrocyte Morphology & Responses to Various Combinations of Growth Factors

Figure 1:
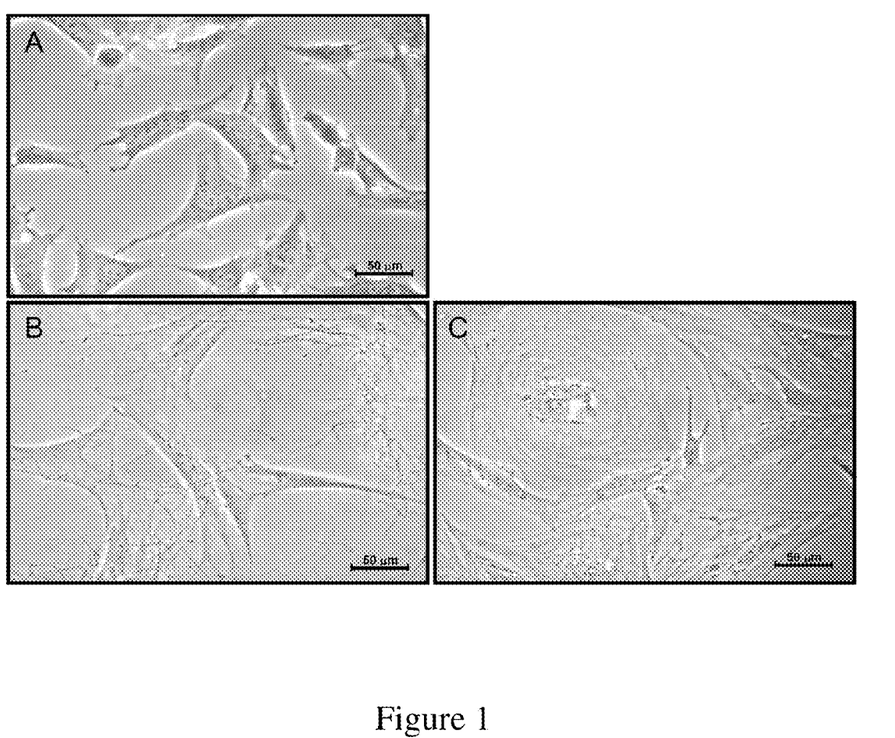
FIG. 1 shows Morphological alterations of rabbit chondrocytes under different culture conditions. The morphology of P1 rabbit chondrocytes were mostly polygonal (A). P9 rabbit chondrocytes with COL II treatment show more polygonal (B) than those of the untreated group, which are fully extended and flattened on the substratum (C).

FIG. 1A shows that P1 chondrocytes appeared polygonal in shape and small in size. In the presence of type II collagen (COL II), stratification was formed in COL II-treated groups, probably through complex cell-matrix interaction. Noteworthy, P9 rabbit chondrocytes cultured in media containing exogenous COL II appeared predominantly polygonal or fibroblast-like (FIG. 1B). However, P9 cells without COL II-supplement became greatly enlarged in size, flattened down on substratum and fully extended, considered as 'rag-like' in general appearance (FIG. 1C).

The effects of combination with cartilaginous growth factors on the induction of GAG expression in rabbit chondrocytes were screened in this study. As this was a preliminary survey, P4 chondrocytes were used. The results were summarized in FIG. 2. In the absence of type II collagen (w/o COL II supplement group), only the treatment of cells with IGF-I plus FGF-2 slightly increased cellular GAG level. However, in the presence of type II collagen (COL II supplement), GAG expression levels of all groups were up-regulated as compared to those of the non-treated control. Among groups of cells supplemented with COL II, the groups treated with either IGF-I plus bFGF or IGF-I plus TGF-β1 showed an increased GAG expression level up to 2 fold as compared to those of the non-treated control, and were significantly higher than those of the COL II-only group.

Figure 2:
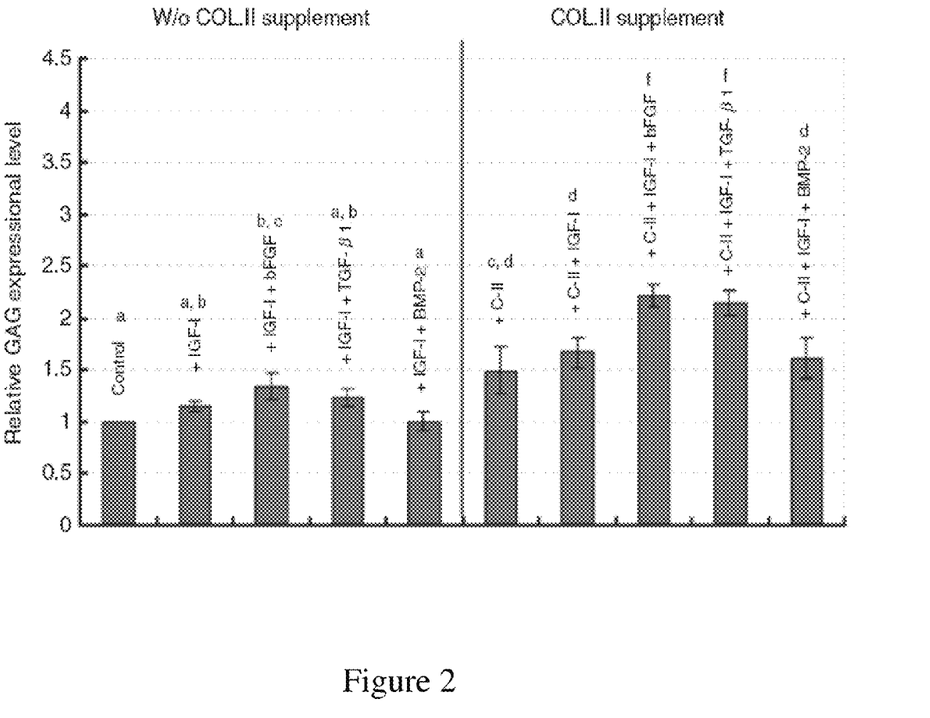
FIG. 2 shows Relative GAG accumulation levels of P4 rabbit chondrocytes treated with various combinations of growth factors with and without type II collagen for 7 days. Data represent means±SD (n=3) as analyzed by ONE WAY ANOVA and Duncan multiple range test. Various serial alphabets indicate the statistical significance of differences at $P<0.05$.

As shown in FIG. 2, the combination of TGF-β1 and IGF-I exhibits the most significant difference in GAG expression between the presence and absence of COL II. A synergistic effect of the combined growth factor treatment and COL II inclusion on chondrocyte phenotype expression was also implicated. Thus, the inclusion of TGF-β1 and IGF-I in basal culture medium was chosen as an optimal condition to study the effect of COL II on the revival/phenotype restoration of quiescent P9 chondrocytes in the subsequent studies.

Example 2

Effects of Type II Collagen on Chondrocyte Proliferation

Figure 3:
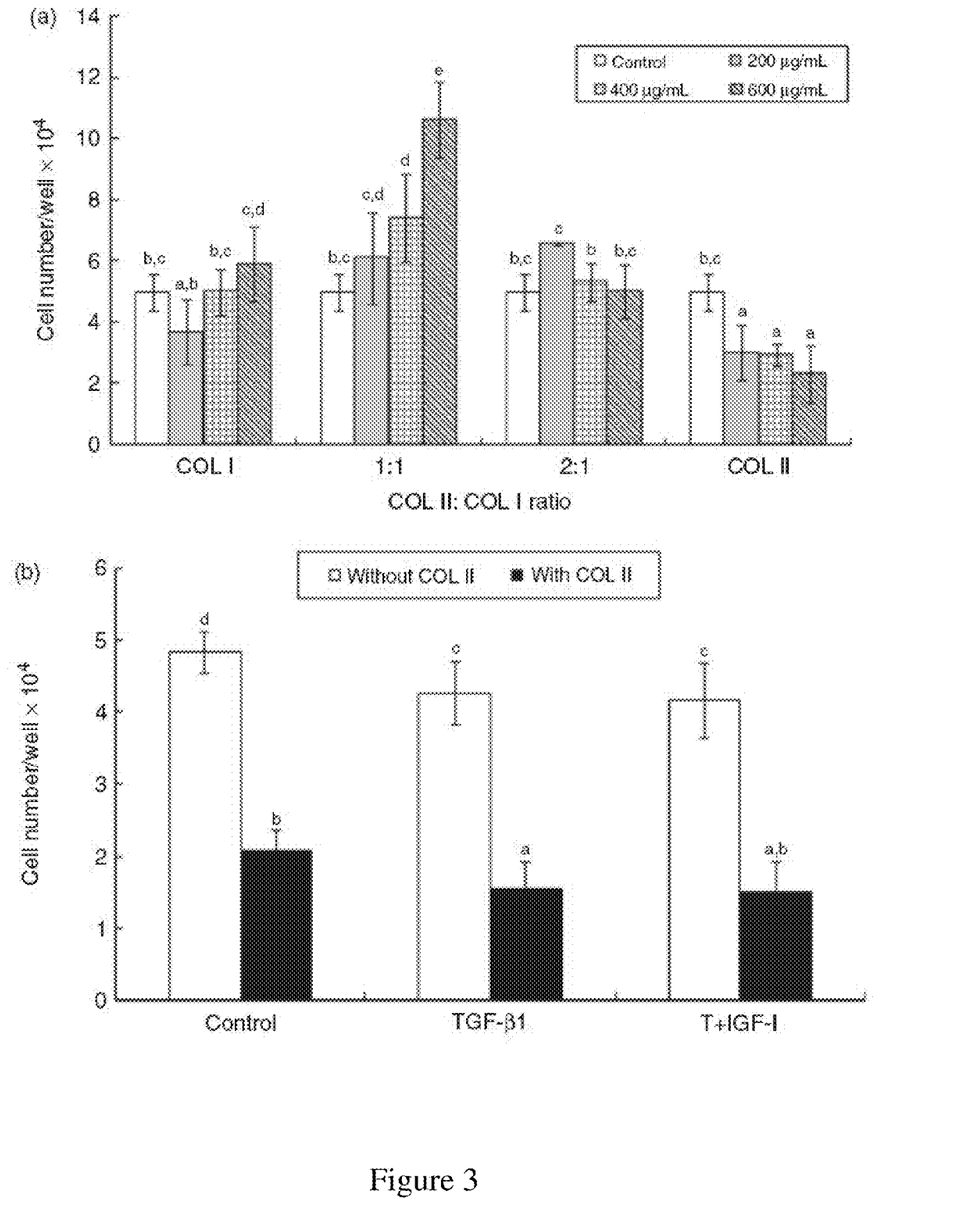
FIG. 3 shows the effects of exogenous collagen and growth factors on cell proliferation rate of P9 rabbit chondrocytes after cultured for 6 days. P9 rabbit chondrocytes cultured in 6 well plates were treated with or without exogenous collagen and in the presence or absence of growth factors for 6 days. (A): The cells in triplicates were cultured in the presence of designated ratio of collagens at indicated concentrations. (B): P9 chondrocytes in triplicates were cultured with or without $TGF-\beta_1$ or $TGF-\beta_1$ plus IGF-I in the presence or absence of COL II (200 µg/ml). Data represent means±SD (n=3) as analyzed by ONE WAY ANOVA and Duncan multiple range test. Various serial alphabets indicate the statistical significance of differences at $P<0.05$.

Among P9 chondrocytes treated with different compositions of ECM components, type I collagen (COL I) alone exhibited little effect on cell proliferation rate except at 600 μg/ml. The effect of combining COL II with COL I at 1:1 ratio on cell proliferation was stimulatory at all three matrix concentrations studied and appeared dose-dependent. At the concentration of 600 μg/ml, the P9 chondrocyte proliferation rate was up to 2.2 folds. In COL II combined with COL I at a ratio of 2:1 group, no significant effect on total cell number were observed when high concentrations of collagen were added. On the contrary, in COL II alone group, COL II greatly inhibited cell proliferation rate at all added concentrations. The final cell number was reduced to 60% and 46%, respectively, of that in the control group when the exogenous COL II concentrations rose from 200 to 600 μg/ml (FIG. 3A).

On the other hand, the proliferation rate of P9 chondrocytes cultured with or without supplementation of exogenous COL II showed disparate growth patterns. In the presence of COL II, chondrocytes proliferated slower than those in the absence of COL II (FIG. 3B). Chondrocytes without exogenous COL II-supplement reached confluence on the fifth day of culture while those in the presence of COL II did not. Furthermore, either TGF-β1 alone or in combination with IGF-I slightly reduced cell proliferation rate no matter in the presence or absence of COL II, as compared to the respective control groups (FIG. 3B).

Example 3

Effects of Type II Collagen on Chondrocytes Glycosaminoglycan Level

Figure 4:
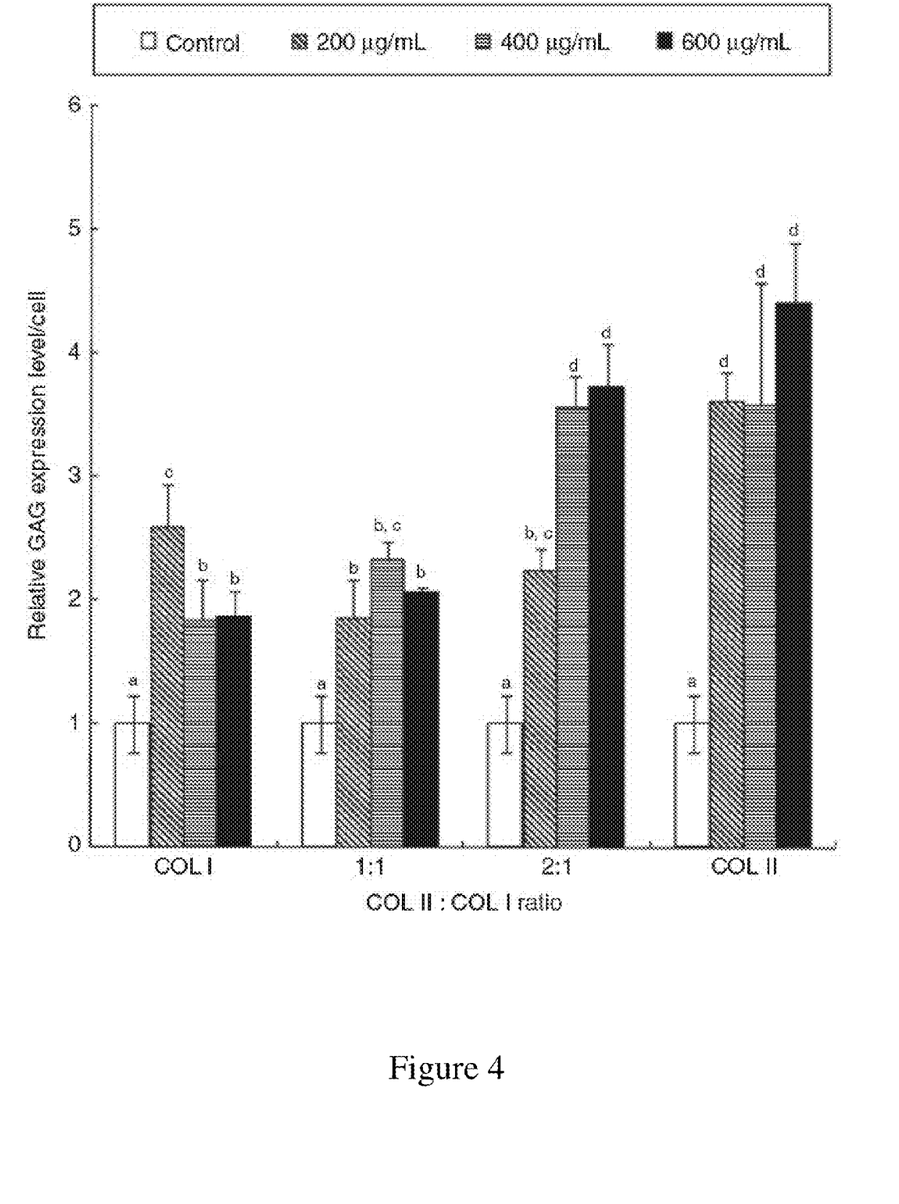
FIG. 4 shows the effects of various combinations of collagens on the accumulated GAG level of P9 rabbit chondrocytes. P9 rabbit chondrocytes cultured in 6 well plates were treated with or without various combinations of exogenous COL I and/or COL II for 6 days. COL I alone, COL II:COL I at 1:1 or 2:1, or COL II alone at 200 µg/ml, 400 µg/ml or 600 µg/ml was included in triplicate dishes for 6 days. The GAG retaining dye was eluted and determined as described in Methods. Data obtained from experiments performed in triplicates were analyzed by ONE WAY ANOVA and Duncan multiple range test and presented as means±SD (n=3). Various serial alphabets indicate the statistical significance of differences at $P<0.05$.

In the group of COL II alone or COL II:COL I at a ratio of 2:1, total GAG levels of P9 chondrocytes were greatly increased up to several folds (3.7 to 4.4 or 2.2 to 3.8 folds, respectively) at all 3 collagen concentrations ranged from 200 to 600 μg/ml (FIG. 4). Nevertheless, in the presence of COL I alone, the total GAG levels of P9 chondrocytes increased only about 1.8 to 2.6 folds with a reverse dose effect. Various concentrations of COL II:COL I at 1:1 ratio also stimulated total GAG levels of chondrocytes to around 1.8 to 2.3 folds (FIG. 4).

Figure 5:
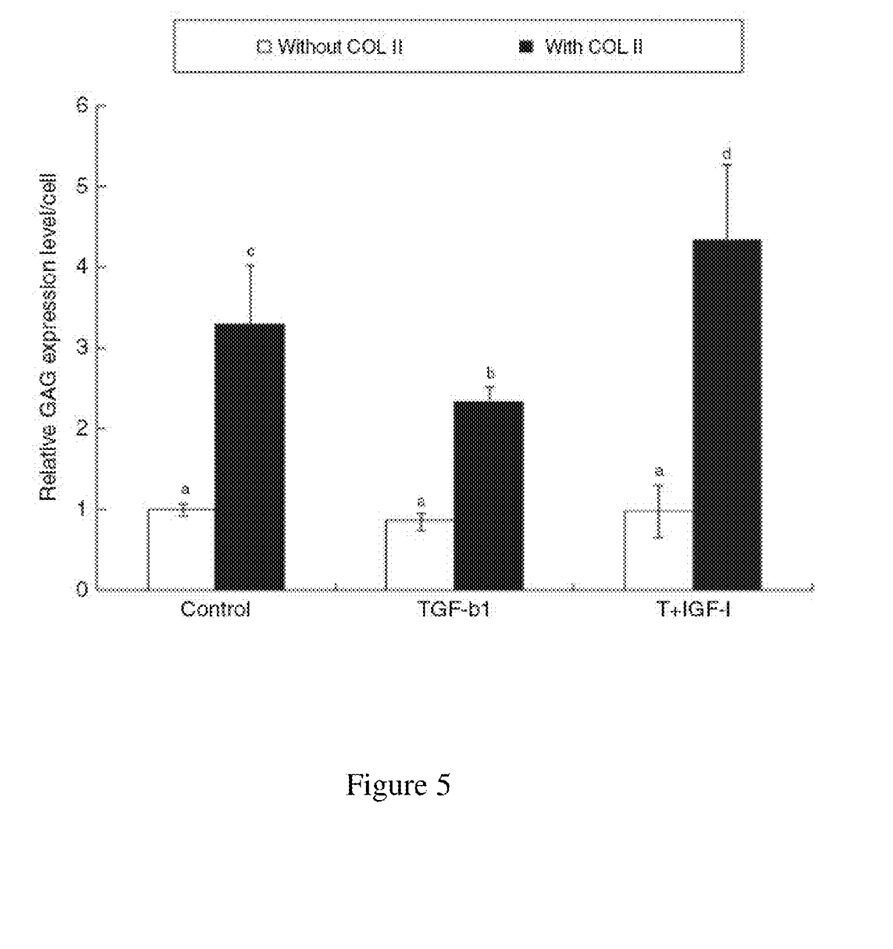
FIG. 5 shows the GAG levels of P9 rabbit chondrocytes after treated with type II collagen and growth factors. P9 rabbit chondrocytes were cultured in 6 well plates in the presence of 200 µg/ml COL II as described in Methods. Cells were either treated with or without TGF-β1 (2 ng/ml) or TGF-β1 (2 ng/ml) plus IGF-I (100 ng/ml) for 6 days. Then, P9 chondrocytes in all groups were stained with alcian blue for GAG accumulation study. Data represent means±SD of triplicate experiments, analyzed by ONE WAY ANOVA and Duncan multiple range test. Various serial alphabets indicate the statistical significance of differences at $P<0.05$.

As shown in FIG. 5, both TGF-β1 and TGF-β1 plus IGF-I affected total GAG levels of P9 chondrocytes in the absence of COL II. On the other hand, in the presence of COL II, TGF-β1 alone slightly but significantly reduced GAG level while IGF-I plus TGF-β1 greatly increased GAG level from that of the TGF-β1 group or COL II alone group. The data clearly demonstrated that in the COL II alone group, COL II effectively promoted the accumulation of GAG level of P9 chondrocytes to 3.3 folds over that of the control. TGF-β1 plus IGF-I but not TGF-β1 alone (only 2.7 folds over control) further enhanced the action of COL II in total GAG levels up to 4.4 fold over the respective control (FIG. 5).

Example 4

Combined Effects of Exogenous Type II Collagen & Growth Factors on Chondrocyte Gene Expression The mRNA levels of type I collagen (COL1A1), type II collagen (COL2A1) and aggrecan (AGN) of dedifferentiated P9 rabbit chondrocytes under various treatment conditions were analyzed by semi-quantitative RT-PCR protocol. To determine the unique role of COL II in regulating chondrocyte differentiation state, the relative cellular mRNA levels of these genes of P9 chondrocytes cultured in the presence or absence of COL II were determined and compared. Cellular COL2A1 mRNA levels of all the COL II-supplemented groups (COL II+), except those cells treated with COL II plus TGF-β1, were significantly increased as compared with the respective control groups without COL II-supplementation (COL II−). The control group without any treatment exhibited little anabolic activity as characterized by trace or non-detectable COL1A1, COL2A1 and AGN mRNA levels (FIG. 6).

Figure 6:
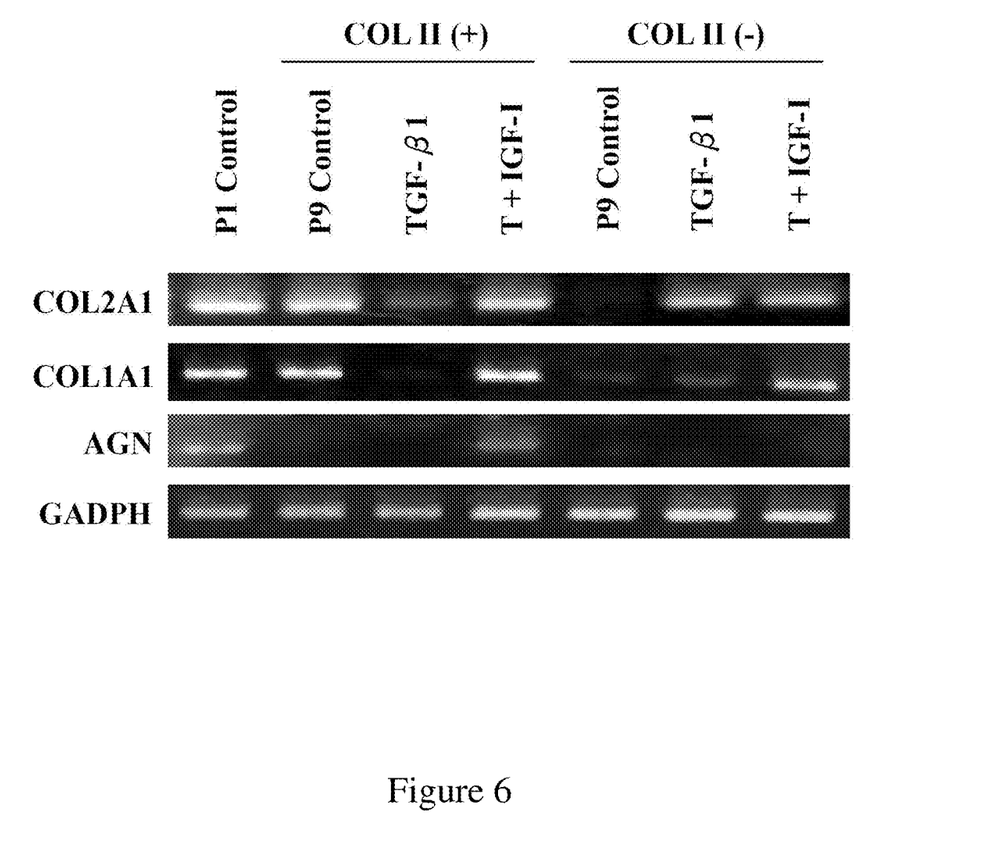

Furthermore, the COL2A1 mRNA levels of P9 rabbit dedifferentiated chondrocytes in growth factor-treated groups (TGF-β1 and TGF-β1+IGF-I) were increased without exogenous COL II treatment (FIG. 6). The combined effects of growth factor(s) and exogenous COL II on COL1A1 and AGN expression in P9 rabbit dedifferentiated chondroctes were also examined. In addition to the ability to up-regulate COL2A1 level, cells treated with COL II alone or its combination with TGF-β1 plus IGF-I also re-established COL1A1 expression. However, only the COL II combined with TGF-β1 and IGF-I group could re-express the AGN mRNA to a similar level as observed in P1 control chondrocytes (FIG. 6).

Figure 7:
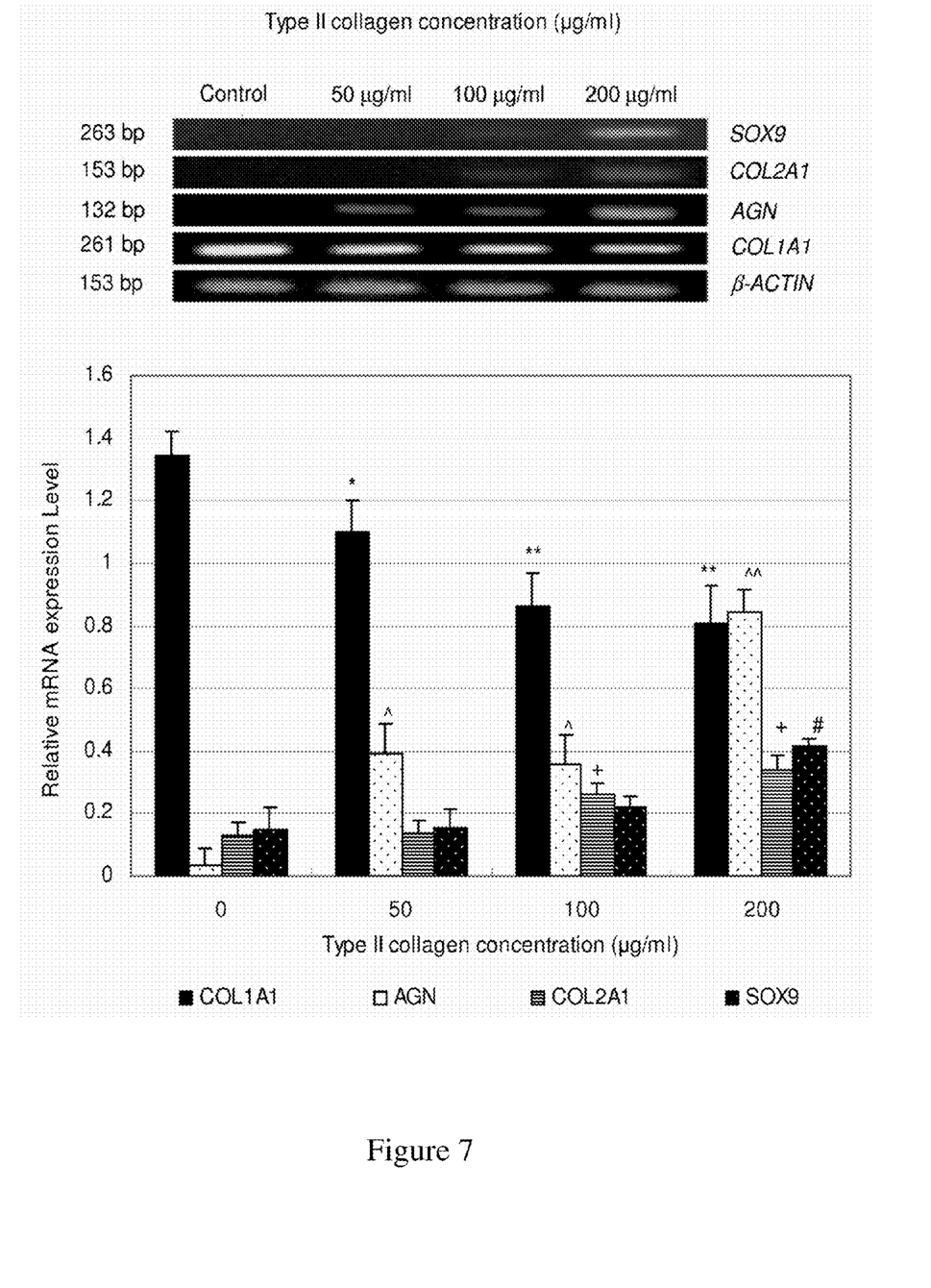
FIG. 7 shows the mRNA expression levels of cartilaginous markers, including Sox9, type II collagen and aggrecan, in P7 human chondrocytes after treated with various concentrations of type II collagen for 12 days. Furthermore, the effect of various concentrations of type II collagen on the mRNA expression level of type I collagen in P7 human chondrocytes is also analyzed.
Figure 8:
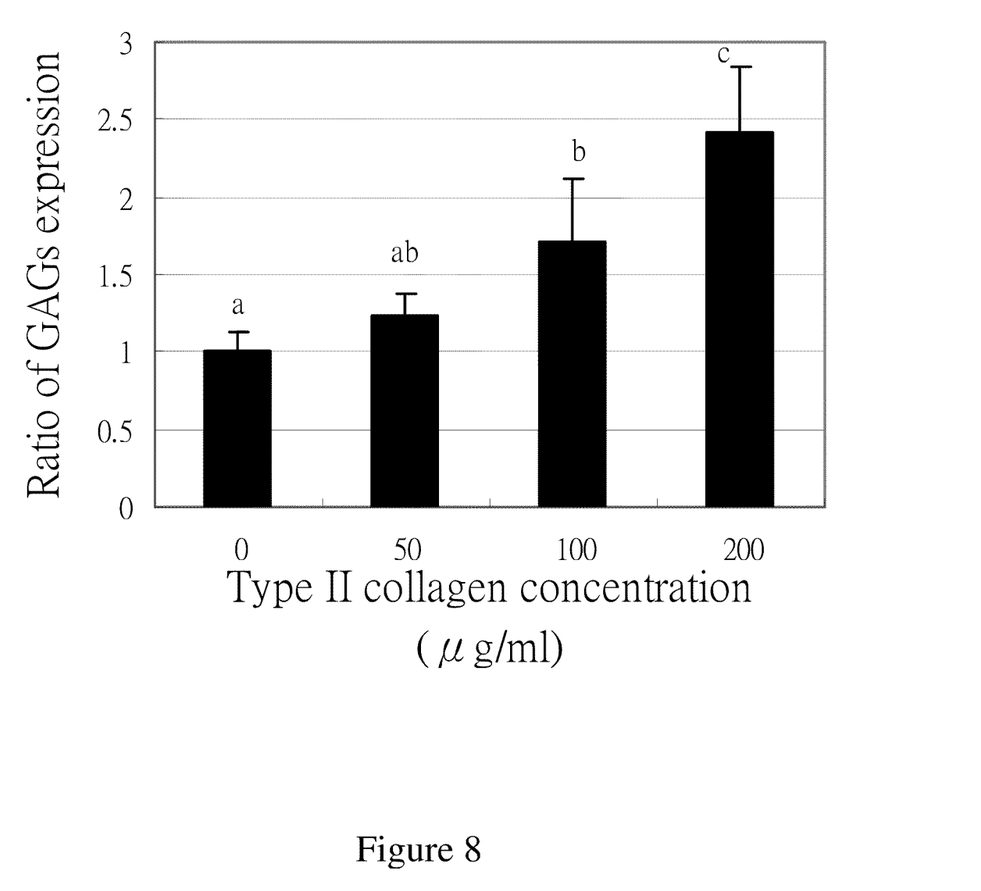
FIG. 8 shows the effect of treatment of exogenous type II collagen at various concentrations for 12 days on GAG level of near quiescent P7 human chondrocytes.

The effect of type II collagen on mRNA expression levels of GAG and other chondrocytic markers, including Sox9, type II collagen and aggrecan in human P7 chondrocytes, were also investigated. The mRNA expression levels of Sox9, type II collagen and aggrecan in P7 human chondrocytes were increased after treated with type II collagen alone (FIG. 7). Furthermore, the mRNA expression level of type I collagen in P7 human chondrocytes is decreased with the treatment with type II collagen. Type II collagen also increases the GAG levels of P7 human chondrocytes (FIG. 8).

Example 5

Redifferentiation of Chondrocytes in Three-Dimensional Cartilaginous Matrix

Figure 9:
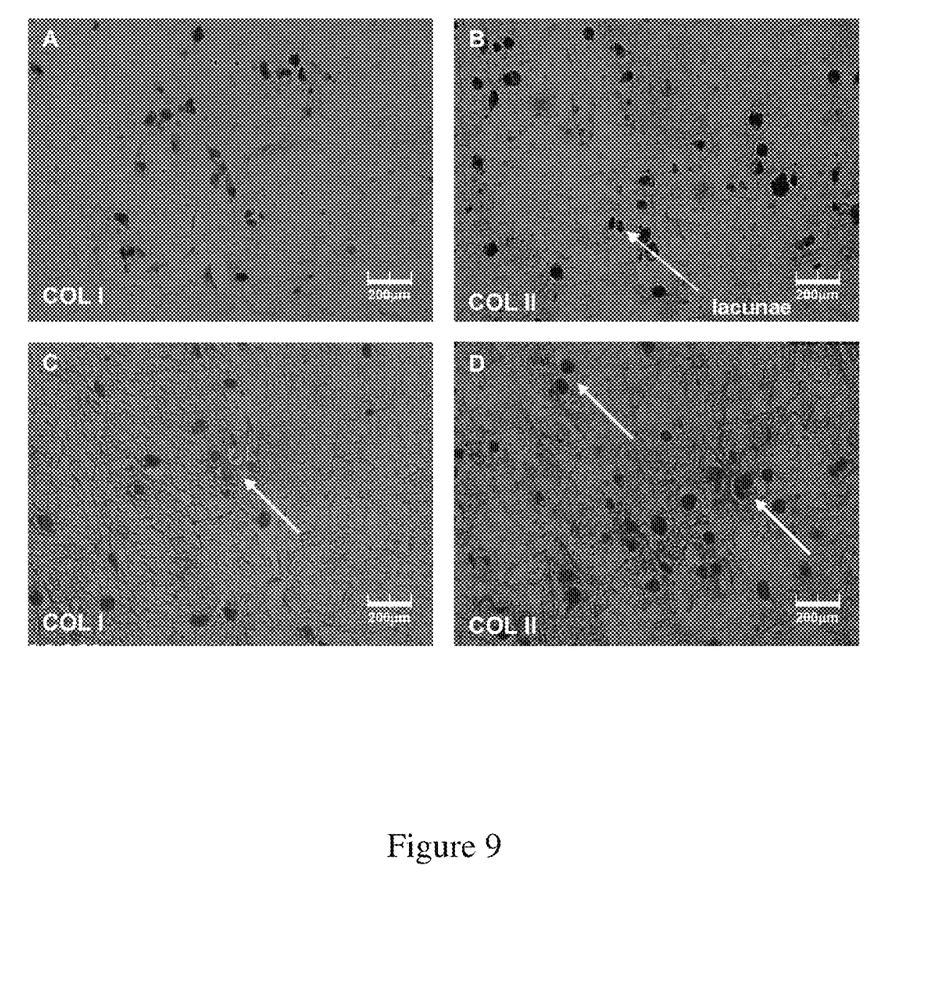
FIG. 9 shows three-dimensional tissue cultivation of P7 human chondrocytes in type I and type II collagen matrices. P7 human chondrocytes were cultured in 3-D collagen gel for 28 days. The histological feature of COL II fabricated 3-D chondrocyte constructs (B) exhibited more lacunae-like cartilaginous feature (arrows) and clustering chondrocytes than did the COL I 3D chondrocyte constructs (A). Furthermore, Safranin O staining of COL II fabricated constructs (D) showed more and thicker red-brown cartilaginous proteoglycan fibers than did the COL I fabricated constructs (C).

The effects of COL I and COL II matrices on the cartilaginous phenotype expression of P7 human chondrocytes were evaluated in the 28-day cultured 3-D constructs. The P7 human chondrocytes in COL II constructs (FIG. 9B) exhibited a more mature cartilaginous features as compared with those cells in the COL I construct (FIG. 9A). A rounder and clustered chondrocyte phenotype was observed in the H/E stained histological section of P7 human chondrocyte-COL II constructs. More cells with lacunae-like structure (arrows), which represent the secreted cartilaginous matrices by the embedded chondrocytes, were observed in the 3D construct made of COL II than in those of COL I constructs. Furthermore, Safranin O stained sections exhibited more and thicker proteoglycan fibers in the section of P7 human chondrocytes-COL II construct (FIG. 9D) than in that of the COL I construct (FIG. 9C). These data indicate that significant richer proteoglycan secretion and matrices deposition occurred in P7 human chondrocytes embedded in COL II than those in the COL I.

REFERENCES

1. Worster A. A., Brent D. Brower-Toland, Lisa A. Fortier, Stephen J. Bent, Janice Williams, Alan J. Nixon, 2001. Chondrocytic differentiation of mesenchymal stem cells sequentially exposed to TGF-β1 in monolayer and IGF-I in a three-dimensional matrix. J Orthopaedic Res. 19:738-749.
2. Brittberg M, Lindahl A, Nilsson A, Ohlsson C, Isaksson O, Peterson L, 1994. Treatment of deep cartilage defects in the knee with autologous chondrocyte transplantation. New Eng J Med. 331:889-941.

3. Convery F R, Akeson Wh, Amiel D, Meyers M H, Monosov A, 1996. Long term survival of chondrocytes in an osteochondral articular cartilage allograft. J Bone Joint Surg. 78-A:1082-1088.
4. Ghazavi M T, Pritzker K P, Davis A M, Gross A E, 1997. Fresh osteochondral allografts for post-traumatic osteochondral defects of the knee. J Bone Joint Surg. 79-B:1008-1013.
5. Benya P D, Padilla S R, Nimmi M E, 1978. Independent regulation of collagen types by chondrocytes during the loss of differentiated function in culture. Cell 15: 1313-1321.
6. Benya, P D, and Shaffer, J. D, 1982. Dedifferentiated chondrocytes reexpress the differentiated collagen phenotype when cultured in agarose gels. Cell 30: 215-224.
7. Martin J A, Buckwalter J A. 1997. Age-related decline in chondrocyte response to insulin-like growth factor-1: the role of growth factor binding proteins. J Orthopaedic Res. 15:491-498.
8. Buckwalter J A, Mankin H J, 2000. The role of chondrocyte-matrix interactions in maintaining and repairing articular cartilage. Biorheology. 37:129-140.
9. Martin J A, Buckwalter J A, 2003. The role of chondrocyte senescence in the pathogenesis of osteoarthritis and in limiting cartilage repair. J Bone Joint Surg. 85: Suppl. 2 106-110.
10. Loeser R F, 2000. Chondrocyte integrin expression and function. Biorheology. 37: 109-116.
11. Tarone G, Hirsch E, Brancaccio M, De Acetis M, Barberis L, Balzac F, et al., 2000. Integrin function and regulation in development. Int J Dev Biol. 44: 725-731.
12. Qi W N, Sean P S, 2003. Type II collagen modulates the composition of extracellular matrix synthesized by articular chondrocytes. J Orthop Res. 21:282-289.
13. Fortier L A, Lust G, Mohammed H O, Nixon A J, 1999. Coordinate upregulation of cartilage matrix synthesis in fibrin cultures supplemented with exogenous insulin-like growth factor-I. J Orthop Res. 17:467-474.
14. Fosang A J, Tyler J A, Hardingham T E, 1991. The effect of interleukin-1 and insulin like growth factor-I on the release of proteoglycan components and hyaluronan from pig articular cartilage in explant culture. Matrix. 11:17-24.
15. Nixon A J, Lillich J T, Burton-Wurster N, Lust G, Mohammed O, 1998. Differentiated cellular function in fetal chondrocytes cultured with insulin-like growth factor-I and transforming growth factor-B. J Orthop Res. 16:531-551.
16. Van Beuningen H M, Arntz O, van den Berg W B, 1993. Insulin-like growth factor stimulation of articular chondrocyte proteoglycan synthesis. Availability and responses at different ages. Br J Rheum. 32:1037-1043.
17. Tsai Y H, Tang J R, Leu B, Liou Y J, Yeh S D, Mao S J T and Lai W F T, 2000. Preparation, characterization and application of purified rabbit type I collagen, type II collagen and their antibodies. Y2K ROC-Japan Joint Symposium on Biomaterials and Controlled Release. 377-380.
18. C. W. Chen, Y. H. Tsai, W. P. Deng, S. N. Shih, C. L. Fang, J. G. Burch, W. H. Chen, and W. F. Lai, 2005. Type I and II collagen regulation of chondrogenic differentiation by mesenchymal progenitor cells. J Orthop Res. 23:446-453
19. Worster A A, Nixon A J, Brower-Toland B D, Williams J, 2000. Effect of transforming growth factor β1 on chondrogenic differentiation of cultured equine mesenchymal stem cells. Am J Vet Res. 61:1003-1010.
20. Hellio Le Graverand M P, Reno C, Hart D A, 2000. Heterogenous response of knee cartilage to pregnancy in the rabbit: assessment of specific mRNA levels. Osteoarthritis Cartilage. 8:53-62.
21. Majima T, Lo I K, Randle J A, Marchuk L L, Shrive N G, Frank C B, Hart D A, 2002. ACL transection influences mRNA levels for collagen type I and TNF-alpha in MCL scar. J Orthop Res. 20:520-525.
22. Watt F M, 1988. Effect of seeding density on stability of the differentiated phenotype of pig articular chondrocytes in culture. J Cell Sci. 89:373-378.
23. Lefebvre V, Peeters-Joris C, Vaes G, 1990. Production of collagens, collagenase and collagenase inhibitor during the dedifferentiation of articular chondrocytes by serial subcultures. Biochim Biophys Acta. 1051:266-275.
24. Thenet S, Benya P D, Demignot S, Feunteun J, Adolphe M, 1992. SV40-immortalization of rabbit articular chondrocytes: alteration of differentiated functions. J Cell Physiol. 150:158-167.
25. Bonaventure J, Kadhom N, Cohen-Solal L, Ng K H, Bourguignon J, Lasselin C, Freisinger P, 1994. Reexpression of cartilage-specific genes by dedifferentiated human articular chondrocytes cultured in alginate beads. Exp Cell Res. 212:97-104.
26. Lemare F, Steimberg N, Le Griel C, Demignot S, Adolphe M, 1998, Dedifferentiated chondrocytes cultured in alginate beads: restoration of the differentiated phenotype and of the metabolic responses to interleukin-1beta. J Cell Physiol. 176:303-313.
27. Wakitani S, Goto T, Young R G, Mansour J M, Goldberg V M, Caplan A I, 1998, Repair of large full-thickness articular cartilage defects with allograft articular chondrocytes embedded in a collagen gel. Tissue Eng. 4:429-444,
28. Talwar R M, Wong B S, Svoboda K, Harper R P, 2006, Effects of estrogen on chondrocyte proliferation and collagen synthesis in skeletally mature articular cartilage. J Oral Maxillofac Surg. 64:600-609
29. O'Leary J M, Hamilton J M, Deane C M, Valeyev N V, Sandell L J, Downing A K, 2004, Solution structure and dynamics of a prototypical chordin-like cysteine-rich repeat (von Willebrand Factor type C module) from collagen IIA. J Biol Chem. 279:53857-53866
30. Yaeger P C, Masi T L, de Ortiz J L, Binette F, Tubo R, McPherson J M, 1997. Synergistic action of transforming growth factor-beta and insulin-like growth factor-I induces expression of type II collagen and aggrecan genes in adult human articular chondrocytes. Exp Cell Res. 237:318-325.
31. Aszodi A, Hunziker E B, Brakebusch C, Fassler R, 2003. Beta1 integrins regulate chondrocyte rotation, G1 progression, and cytokinesis. Genes Dev. 17:2465-2479.
32. Segat D, Comai R, Di Marco E, Strangio A, Cancedda R, Franzi A T, Tacchetti C, 2002. Integrins alpha(6A)beta 1 and alpha(6B)beta 1 promote different stages of chondrogenic cell differentiation. J Biol Chem. 277:31612-31622.
33. Knight C G, Morton L F, Onley D J, Peachey A R, Messent A J, Smethurst P A, Tuckwell D S, Farndale R W, Barnes M J, 1998. Identification in collagen type I of an integrin alpha2 beta1-binding site containing an essential GER sequence. J Biol Chem. 273:33287-33294.

What is claimed is:

1. A method for restoring native chondrocyte phenotype and functions of, and/or increasing type II collagen and Aggrecan (AGN) expression levels and Glycosaminoglycan (GAG) accumulation level in dedifferentiated chondrocytes which have been subcultured and expanded in vitro, comprising culturing the said dedifferentiated chondrocytes in vitro with a medium comprising type II collagen, wherein the dedifferentiated chondrocytes are the chondrocytes which have lost their chondrocyte phenotype to become dedifferentiated chondrocytes after they have been subcultured for more than three, four, five, six and up to eight or more passages.

2. The method according to claim 1, wherein one or more growth factor(s) are further added to the medium with type II collagen to improve the restoration extent of phenotype and functions of the said dedifferentiated chondrocytes, and/or increase type II collagen and AGN expression level and GAG accumulation level in the dedifferentiated chondrocytes.

3. The method of claim 2, wherein the growth factor is selected from the group consisting of bone morphogenetic proteins (BMP), transforming growth factor (TGF), insulin-like growth factors (IGF), fibroblast growth factor (FGF), platelet-derived growth factor (PDGF), growth/differentiation factor (GDF), vascular endothelial growth factor (VEGF) and the combinations thereof.

4. The method of claim 3, wherein the growth factor is selected from the group consisting of transforming growth factors (TGF), insulin-like growth factors (IGF), fibroblast growth factors (FGF), bone morphogenetic proteins (BMP) or the combination thereof.

5. The method of claim 3, wherein the growth factor is selected from the group consisting of insulin-like growth factor (IGF), transforming growth factor (TGF), fibroblast growth factor (FGF), IGF in combination with TGF and/or with FGF, and IGF-1 in combination with TGF-β1 and/or FGF-2.

6. The method of claim 1, wherein type I collagen is further included in the medium to increase the proliferation of chondrocytes and total GAG expression level of the dedifferentiated chondrocytes.

7. The method of claim 6, wherein the ratio of type I to type II collagen ranges from 1:1 to 0.1:9.9.

8. The method of claim 6, wherein the ratio of type I to type II collagen is from 1:2 to 0.1:9.9.

9. The method of claim 6, the ratio of type I to type II collagen is 1:2 to 1:6, 1:2 to 1:5, 1:2 to 1:4 or 1:2 to 1:3.

10. The method of claim 1, wherein the dedifferentiated chondrocytes are cultured with type II collagen in two-dimensional (2D) or three-dimensional (3D) cell culture.

11. The method of claim 1, wherein the dedifferentiated chondrocytes have been subcultured and expanded in vitro from the chondrocytes which can be isolated from human, orangutan, monkey, chimpanzee, dog, cat, rat, rabbit, mouse, horse, cow, pig, sheep or transgenic animal.

12. The method of claim 1, wherein the medium is selected from the group consisting of Dulbecco's Modified Eagle's Medium (DMEM), Dulbecco's Modified Eagle's Medium/Ham's Nutrient Mixture F12 (DMEM/F12), alpha modified Minimal Essential Medium (α-MEM), and Roswell Park Memorial Institute Media 1640 (RPMI Media 1640).

13. The method of claim 1, wherein the method produces redifferentiated chondrocytes which have native chondrocyte phenotype including (i) a spherical shape and (ii) an increased expression level of AGN, GAG, and type II collagen and decreased level of type I collagen, and can be used in cartilage repair or the treatment of cartilaginous defects.

14. The method of claim 1, wherein the concentration of type II collagen ranges from 50 to 1,000 μg/ml.

15. The method of claim 1, wherein the concentration of type II collagen ranges from 50 to 400 μg/ml.

16. The method of claim 15, wherein the concentration of type II collagen is 200 to 400 μg/ml.

17. A medium for restoring native chondrocyte phenotype and functions of, and/or increasing type II collagen and AGN expression levels and GAG accumulation level in the dedifferentiated chondrocytes which have been subcultured and expanded in vitro, comprising a medium used to subculture and expand chondrocytes and type II collagen wherein the concentration of type II collagen ranges from 50 to 400 μg/ml.

18. The medium of claim 17, wherein the concentration of type II collagen is 200 to 400 μg/ml.

19. The medium of claim 17, wherein the medium further comprises one or more growth factor(s) as defined in claim 3 and/or type I collagen.

20. A kit for restoring native chondrocyte phenotype and functions of, and/or increasing type II collagen and AGN expression levels and GAG accumulation level in dedifferentiated chondrocytes which have been subcultured and expanded in vitro, which comprises the medium of claim 17.

* * * * *